United States Patent [19]
Muni et al.

[11] Patent Number: 5,533,968
[45] Date of Patent: Jul. 9, 1996

[54] LOW PROFILE CATHETER WITH EXPANDABLE OUTER TUBULAR MEMBER

[75] Inventors: Ketan P. Muni, San Jose; Motasim M. Sirhan, Newark, both of Calif.

[73] Assignee: Advanced Cardiovascular Systems, Inc., Santa Clara, Calif.

[21] Appl. No.: 250,809

[22] Filed: May 27, 1994

Related U.S. Application Data

[63] Continuation-in-part of Ser. No. 921,304, Jul. 28, 1992, abandoned, which is a continuation-in-part of Ser. No. 758,630, Sep. 12, 1991, abandoned, and a continuation-in-part of Ser. No. 155,084, Nov. 19, 1993, abandoned, which is a continuation of Ser. No. 853,039, Mar. 17, 1992, abandoned, which is a continuation-in-part of Ser. No. 700,617, May 15, 1991, abandoned.

[51] Int. Cl.⁶ ..................................................... A61M 29/00
[52] U.S. Cl. .............................. 604/96; 604/102; 606/194
[58] Field of Search .............................. 604/96–103, 280, 604/282; 606/192–196; 600/18

[56] References Cited

U.S. PATENT DOCUMENTS

| | | |
|---|---|---|
| 3,769,981 | 11/1973 | McWhorter . |
| 3,978,863 | 9/1976 | Fettel et al. . |
| 4,406,656 | 9/1983 | Hattler et al. . |
| 4,484,579 | 11/1984 | Meno et al. . |
| 4,601,713 | 7/1986 | Fuqua . |
| 4,776,841 | 10/1988 | Catalano . |
| 4,820,349 | 4/1989 | Saab ........................................ 606/194 |
| 4,892,519 | 1/1990 | Songer et al. . |
| 5,040,548 | 8/1991 | Yock . |
| 5,106,368 | 4/1992 | Uldall et al. . |
| 5,154,725 | 10/1992 | Leopold . |
| 5,171,222 | 12/1992 | Euteneuer et al. . |

FOREIGN PATENT DOCUMENTS

| | | |
|---|---|---|
| 197787 | 10/1986 | European Pat. Off. . |
| 0304258 | 2/1989 | European Pat. Off. . |
| 3742710 | 7/1989 | Germany . |

*Primary Examiner*—John D. Yasko
*Assistant Examiner*—Adam J. Cermak
*Attorney, Agent, or Firm*—Crosby, Heafey, Roach & May

[57] ABSTRACT

An intravascular catheter such as a dilatation catheter for angioplasty with a catheter shaft having an outer tubular member with an expandable distal section which expands elasticly upon the introduction of fluid under a pressure within a first pressure range to a larger diameter and which contracts by elastic recoil upon the withdrawal of the inflation fluid. The expandable distal section is relatively noncompliant at pressures above the first pressure range. Preferably, the dilatation catheter has an inflatable member or balloon disposed distal to the expandable distal section which is formed of the same polymeric material as the expandable distal section and is in fluid communication with the expandable inner lumen within the expandable distal section. In one preferred embodiment the catheter has a distal section which includes an outer tubular member bonded or otherwise secured (e.g. heat bonding or adhesive bonding) to an inner tubular member over a length to provide a catheter shaft having small transverse dimensions and improved flexibility with no loss in pushability. The unbonded or unsecured portion of the outer tubular member is expandable and when expanded forms with the inner tubular member an inflation lumen in fluid communication with the interior of the balloon.

27 Claims, 4 Drawing Sheets

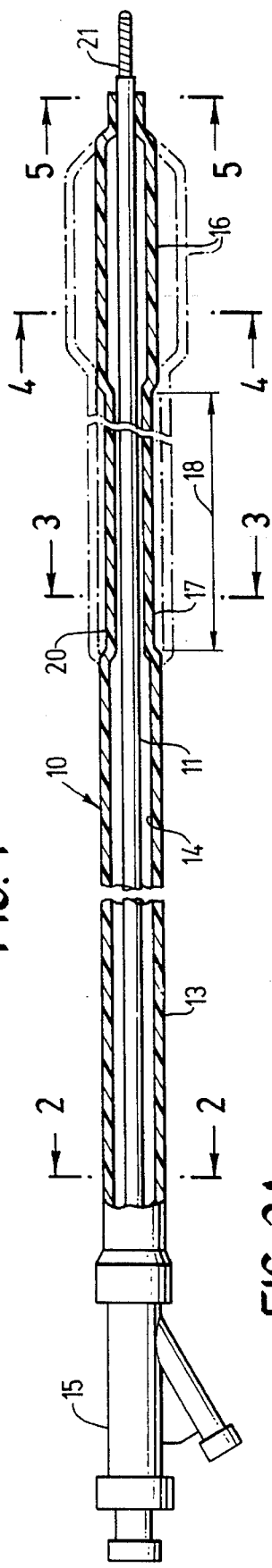
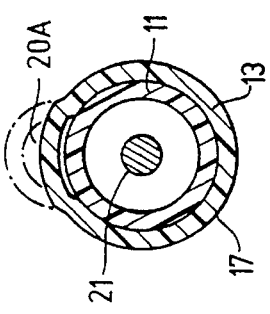
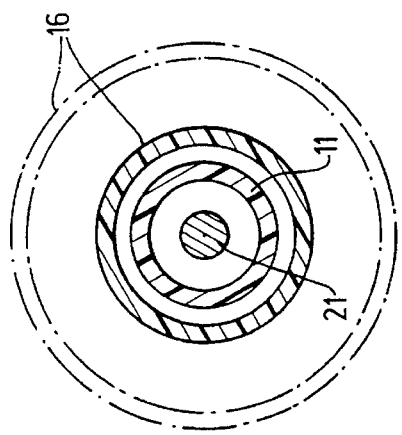
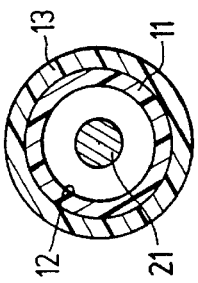

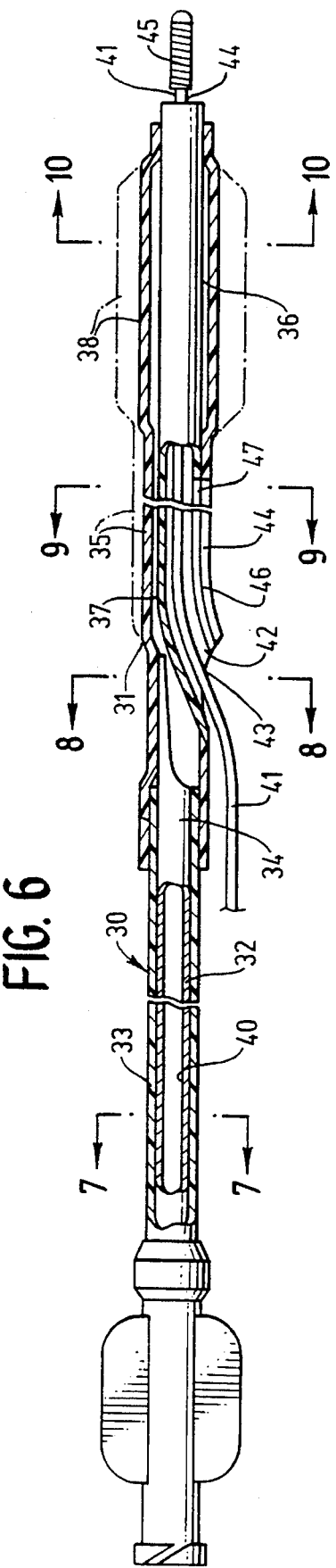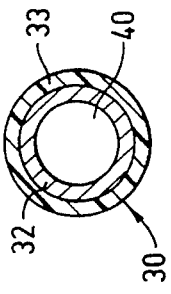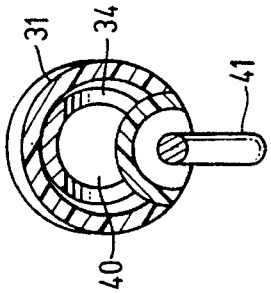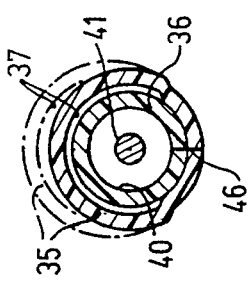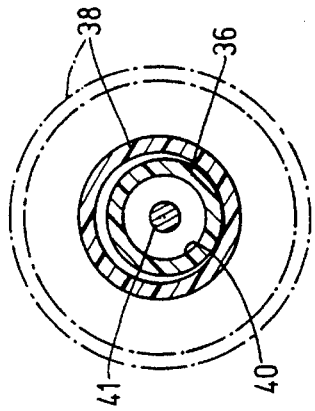

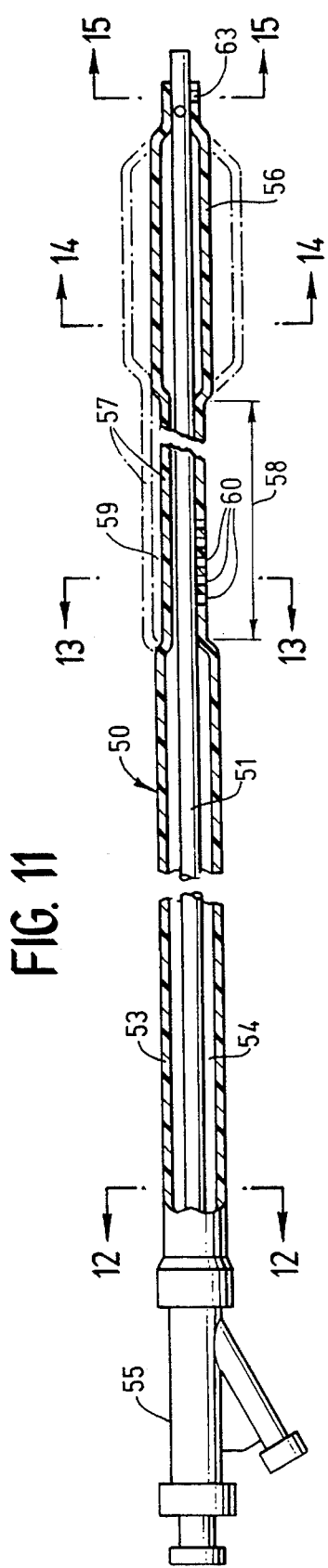
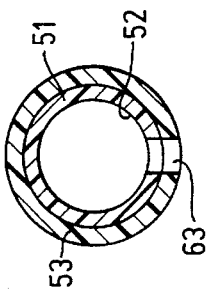
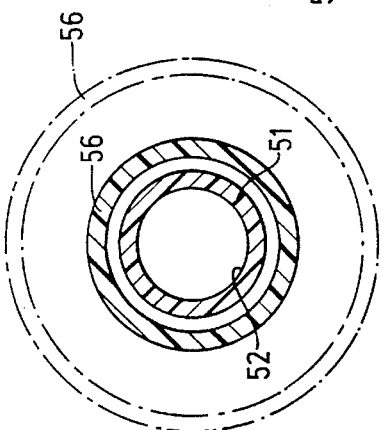
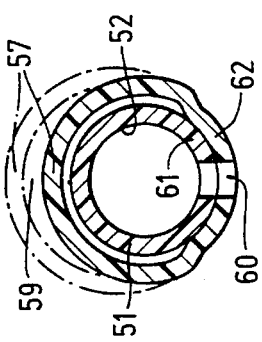
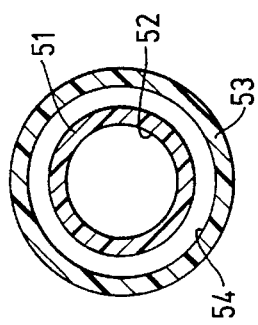

LOW PROFILE CATHETER WITH EXPANDABLE OUTER TUBULAR MEMBER

RELATED APPLICATIONS

This application is a continuation-in-part of application Ser. No. 07/921,304, filed on Jul. 28, 1992, entitled LOW PROFILE CATHETER WITH EXPANDABLE OUTER TUBULAR MEMBER (abandoned), which is a continuation-in-part of application Ser. No. 07/758,630, filed on Sep. 12, 1991, entitled FORMED IN PLACE BALLOON FOR VASCULAR CATHETER (abandoned), and a continuation-in-part of application Ser. No. 08/155,084, filed on Nov. 19, 1993, entitled LOW PROFILE CATHETER WITH EXPANDABLE INFLATION LUMEN (now abandoned) which is a continuation of Ser. No. 07/853,039, filed on Mar. 17, 1992, entitled LOW PROFILE CATHETER WITH EXPANDABLE INFLATION LUMEN (abandoned) which is a continuation-in-part of application Ser. No. 07/700,617, filed on May 15, 1991, entitled LOW PROFILE DILATATION CATHETER (abandoned).

BACKGROUND OF THE INVENTION

This invention generally relates to intravascular catheters, such as balloon dilatation catheters used in percutaneous transluminal coronary angioplasty (PTCA).

PTCA is a widely used procedure for the treatment of coronary heart disease wherein a balloon dilatation catheter is advanced into the patient's coronary artery and a balloon on the distal end of the catheter is inflated within the stenotic region of the patient's artery to open up the arterial passageway and thereby increase the blood flow therethrough. To facilitate the advancement of the dilatation catheter into the patient's coronary artery, a guiding catheter having a preshaped distal tip is first percutaneously introduced into the cardiovascular system of a patient by the Seldinger technique through the brachial or femoral arteries and is advanced therein until the preshaped distal tip of the guiding catheter is disposed within the aorta adjacent the ostium of the desired coronary artery. The guiding catheter is twisted or torqued from its proximal end, which extends out of the patient, to guide the distal tip of the guiding catheter into the desired ostium. A balloon dilatation catheter may then be advanced through the inner lumen of the guiding catheter into the patient's coronary artery until the balloon on the dilatation catheter is disposed within the stenotic region of the patient's artery. The balloon is inflated and deflated one or more times to open up the arterial passageway and increase the flow of blood.

One type of catheter frequently used in PTCA procedures is an over-the-wire type balloon dilatation catheter. Commercially available over-the-wire type dilatation catheters include the SIMPSON ULTRA LOW PROFILE (TM), the HARTZLER ACX (R), the HARTZLER ACX II (TM), the PINKERTON 0.018 (TM) and the ACS TEN (TM) balloon dilatation catheters sold by the assignee of the present invention, Advanced Cardiovascular Systems, Inc. (ACS).

Another type of over-the-wire dilatation catheter is the rapid exchange type catheter, which was introduced by ACS under the trademark ACS RX® Coronary Dilatation Catheter. It is described and claimed in U.S. Pat. No. 5,040,548 (Yock), U.S. Pat. No. 5,061,273 (Yock), U.S. Pat. No. 4,748,982 (Horzewski et al.) and U.S. Pat. No. 5,154,725 (Leopold) which are incorporated herein by reference. This dilatation catheter has a short guidewire receiving sleeve or inner lumen extending through a distal portion of the catheter. The sleeve or inner lumen extends proximally from a first guidewire port in the distal end of the catheter to a second guidewire port in the catheter spaced proximally from the inflatable member of the catheter. A slit may be provided in the wall of the catheter body which extends distally from the second guidewire port, preferably to a location proximal to the proximal end of the inflatable balloon. The structure of the catheter allows for the rapid exchange of the catheter without the need for an exchange wire or adding a guidewire extension to the proximal end of the guidewire.

Some over-the-wire type dilatation catheters have perfusion capabilities where one or more perfusion ports are provided proximal to the dilatation balloon in fluid communication with an guidewire receiving inner lumen extending to the distal end of the catheter and one or more perfusion ports are preferably provided in the catheter, distal to the balloon in fluid communication with the guidewire receiving inner lumen. When the balloon of a dilatation catheter with perfusion capabilities is inflated to dilate a stenosis, oxygenated blood in the artery or the aorta or both, depending upon the location of the dilatation catheter within the coronary anatomy, is forced to pass through the proximal perfusion ports, through the guidewire receiving inner lumen of the catheter and out the distal perfusion ports. The flow of oxygenated blood downstream from the inflated balloon minimizes ischemic conditions in tissue distal to the balloon and allows for long term dilatations, e.g. 30 minutes or even several hours or more. Commercially available perfusion type dilatation catheters include the STACK PERFUSION (TM) and the ACS RX PERFUSION (TM) dilatation catheters which are sold by ACS.

A continual effort has been made in the development of intravascular catheters, particularly angioplasty catheters, to reduce the transverse dimensions or profile of such catheters without detrimentally affecting the pushability and other characteristics of the catheters, particularly in the distal portion of the catheters. A balloon dilatation catheter with a reduced profile and an increase or no loss in pushability allow an the catheter to be advanced much further into a patient's vasculature and to cross much tighter lesions.

Despite the many technical advances in these areas, the need for intravascular catheters having even lower distal profiles with excellent flexibility and pushability remains. The present invention satisfies these and other needs.

SUMMARY OF THE INVENTION

The present invention is directed to a dilatation catheter having a low profile catheter shaft, particularly in the distal portion thereof, with improved flexibility and pushability.

The catheter shaft of the invention generally includes, at least in a distal portion thereof, an expandable outer tubular member defining an inner lumen and an inflatable member distal to the expandable outer tubular member. The outer tubular member in the distal section is formed of polymer material which allows it to expand to a larger diameter in an elastic mode to facilitate the flow of inflation fluid to the interior of the inflatable member on the distal end of catheter shaft when it is inflated. Upon deflation, the expanded outer tubular member contracts by elastic recoil to a diameter substantially smaller than the expanded diameter thereof.

The distal section of the outer tubular member expands significantly when the internal pressure is within a first pressure range. However, when the internal pressure is within a second higher pressure range, the expansion is very limited because the distal section is relatively noncompliant. The expansion at the second higher pressure level, while limited, is directly related to the internal pressure, i.e, it is elastic, and can be readily controlled by regulating the pressure. The first pressure range where substantial expansion occurs may be significantly higher than atmospheric pressure and in this instance there may be insignificant expansion until the internal pressure reaches the first pressure range. The expansion of the distal section at failure within the second higher pressure range should not be more than about 25%, preferably not more than about 10%, of the maximum diameter of the distal section at the maximum pressure within the first pressure range. Upon deflation, the distal section contracts to a diameter much smaller than the inflated diameters by means of elastic recoil and thereby provides for a rapid and complete deflation of the inflatable member. The first pressure range may extend from about 4 to about 14 atmospheres, preferably about 7 to about 12 atmospheres for polyolefinic ionomer materials described hereinafter, and the second pressure range may extend from about 8 to about 25 atmospheres, preferably about 10 to about 20 atmospheres for polyolefinic ionomer materials. Other materials may have other pressure ranges.

In some of the presently preferred embodiments of the invention, only a distal portion of the outer tubular member is expandable. The length of the expandable distal section of these embodiments may range from about 5 mm to about 40 cm or more, and preferably ranges from about 2 to about 30 cm. In some instances the outer tubular member may be expandable along its entire length or any portion thereof.

As discussed above, the distal section of the outer tubular member is preferably formed of polymer material which allows a significant elastic expansion when inflation fluid under elevated pressure is introduced into the lumen defined at least in part by the distal section of the outer tubular member. Beyond a particular expansion, the distal section has a very limited compliance which ensures that the catheter shaft is not over inflated. The expandable portion of the outer tubular member is formed from a heat shrinkable thermoplastic polymer material, particularly an irradiated cross-linked polymer material, which has been thermally treated to a temperature of not more than about 75° C., preferably not more than about 50° C., above or below the crystalline melting point of the polymer to provide the desired expansion. It is preferred to expand the expandable distal section at the thermal treatment temperature, cool and then heat shrink the expanded distal section at a temperature within about 45° C. to about 80° C. to a diameter much smaller than the expanded diameter. Particularly suitable polymer materials for the expandable portion of the outer tubular member are polyolefinic ionomers selected from the group consisting of sodium, lithium and zinc ionomers as described in copending application Ser. No. 07/758,630, filed Sep. 12, 1991, entitled FORMED IN PLACE BALLOON FOR VASCULAR CATHETER. The preferred polyolefinic ionomers include those sold under the trademark Surlyn® by E. I. DuPont, deNemours & Co. and particularly zinc ionomers 8020/IBE and 9020, sodium ionomers 8920 and 8940 and lithium ionomers 7930 and 7940 (DuPont product designations). Other suitable heat shrinkable polymers include ethylene vinyl acetate such as ELVAX® sold by E. I. DuPont, deNemours & Co. The expandable distal section of the outer tubular member and the inflatable member may be formed from the same tubular element, with the different portions of the tubular element being given thermomechanical processing to provide the desired characteristics, as will be described subsequently. The ionomer material may be extruded at a temperature between about 250° F. to about 500° F., preferably about 350° F. to about 450° F.

One presently preferred embodiment of the intravascular catheter of the invention includes an elongated catheter shaft which has at least in a distal portion thereof an inner tubular member and an outer tubular member disposed about the inner member with a substantial portion of the outer tubular member along a length thereof taking the shape of and being secured or bonded to the exterior of an underlying portion of the inner tubular member and with a minor portion of the outer tubular member along said length coextensive with the secured portion being unsecured to the underlying inner tubular member and thereby defining with the inner tubular member an inflation lumen along said unsecured length. The outer tubular member in the unsecured length expands upon inflation to allow inflation fluid to flow to the interior of the inflatable member on the distal end of catheter shaft. The compliant unsecured portion of the outer tubular member along the length expands significantly along the length when the interior pressure exceeds a particular level to allow for the rapid inflation and deflation of the inflatable member.

At least about 30% but not more than about 90%, preferably not more than about 80%, of the area of the inner surface of the outer tubular member takes the shape of and is secured to the inner tubular member. The length of the secured section of the outer tubular member may range from about 5 mm to about 40 cm or more, but preferably ranges from about 2 to about 35 cm. While in some of the presently preferred embodiments of the invention only a distal portion of the outer tubular member takes the shape of and is secured to the inner tubular member, in some instances the outer tubular member may be secured to the underlying inner member along its entire length. The bond or other connection between the inner and outer tubular members need not be continuous along the entire secured length, but may be intermittent along the said length, so long as a significant portion thereof is bonded or otherwise secured to the underlying inner tubular member to ensure that the requisite portion of the outer tubular member takes the shape of the inner tubular member. The outer tubular member may be secured to the inner tubular member by heat or fusion bonding, adhesive bonding, heat shrinking the outer tube onto the inner tube or other suitable means.

The invention provides substantial reductions in the transverse dimensions of the catheter shaft. Minimum transverse dimensions of expandable distal sections of the outer tubular members designed for coronary dilatation catheters are on the order of about 0.02 to about 0.06 inch (0.51–1.5 mm). For peripheral arteries the transverse dimensions may be larger. Preferably, the deflated transverse dimension of the expandable distal section of the outer tubular member is essentially the same or just slightly smaller than the deflated transverse dimension of the inflatable member so as to present a distal portion of the catheter with a smooth exterior surface which facilitates the passage of the distal portion through tortuous anatomy. The catheter provides improved flexibility with little or no loss in pushability.

The improvements of the invention are applicable to a wide variety of intravascular catheters and to essentially all types of dilatation catheters with inflatable or expandable members, such as those described in the BACKGROUND OF THE INVENTION. These and other advantages of the invention will become more apparent from the following detailed description of the invention when taken in conjunction with accompanying exemplary drawings.

BRIEF DESCRIPTION OF THE DRAWINGS

FIG. 1 is an elevational view, partially in section, of a balloon dilatation catheter embodying features of the invention.

FIG. 2 is a transverse cross-sectional view of the catheter shown in FIG. 1 taken along the lines 2—2.

FIG. 3 is a transverse cross-sectional view of the catheter shown in FIG. 1 taken along the lines 3—3.

FIG. 3A is an transverse cross-sectional view of an alternative catheter construction, similar to the catheter shown in FIG. 1 and taken at essentially the same location as FIG. 3.

FIG. 4 is a transverse cross-sectional view of the catheter shown in FIG. 1 taken along the lines 4—4.

FIG. 5 is a transverse cross-sectional view of the catheter shown in FIG. 1 taken along the lines 5—5.

FIG. 6 is an elevational view, partially in section, of a dilatation catheter embodying features of the invention which is adapted for rapid exchange during an intravascular procedure.

FIG. 7 is a transverse cross-sectional view of the catheter shown in FIG. 6 taken along the lines 7—7.

FIG. 8 is a transverse cross-sectional view of the catheter shown in FIG. 6 taken along the lines 8—8.

FIG. 9 is a transverse cross-sectional view of the catheter shown in FIG. 6 taken along the lines 9—9.

FIG. 10 is a transverse cross-sectional view of the catheter shown in FIG. 6 taken along the lines 10—10.

FIG. 11 is an elevational view, partially in section, of a dilatation catheter embodying features of the invention which is adapted to perfuse oxygenated blood distal to the inflated balloon of the catheter during an intravascular procedure.

FIG. 12 is a transverse cross-sectional view of the catheter shown in FIG. 11 taken along the lines 12—12.

FIG. 13 is a transverse cross-sectional view of the catheter shown in FIG. 11 taken along the lines 13—13.

FIG. 14 is a transverse cross-sectional view of the catheter shown in FIG. 11 taken along the lines 14—14.

FIG. 15 is a transverse cross-sectional view of the catheter shown in FIG. 11 taken along the lines 15—15.

DETAILED DESCRIPTION OF THE INVENTION

Figure 16:
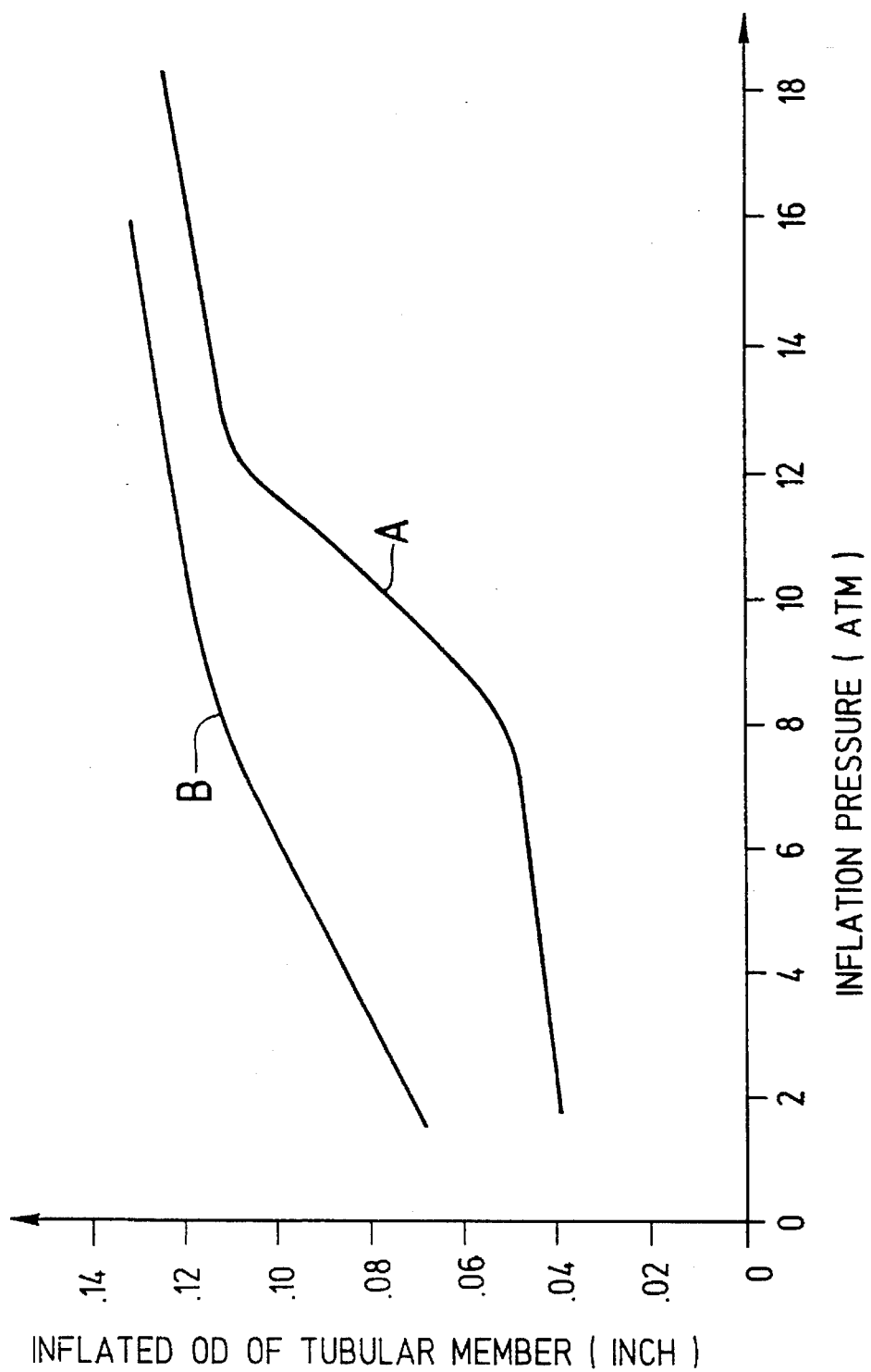
FIG. 16 is a graphical representation of the expansion of two embodiments of the outer tubular member of the invention.

FIGS. 1–5 schematically illustrate an over-the-wire dilatation catheter embodying features of the invention. The catheter includes an elongated catheter shaft 10 which has an inner tubular member 11 with a guidewire receiving inner lumen 12, an outer tubular member 13 disposed about the inner tubular member and defining therebetween annular inflation lumen 14 which extends through the proximal portion of the catheter shaft. An adapter 15 is secured to the proximal ends of the inner and outer tubular members 11 and 13. An inflatable member or balloon 16 is formed as part of the outer tubular member 13 with the distal end of the inflatable member secured to the distal end of the inner tubular member 11. The inflatable member 16 and the distal expandable portion 17 of the shaft 10 may be formed from the same tubing as the proximal portion of the outer tubular member 13 as shown in FIG. 1 or they may be made separately and secured to the distal end of the proximal portion of the outer tubular member.

The inflatable member 16 preferably has essentially the same or, as shown in the drawings, slightly larger transverse dimensions as the distal expandable section 17 of the outer tubular member 13. The distal section 17 along the length 18 when in the deflated condition forms a very thin inflation lumen 20 having an circular transverse cross-section, as shown in FIG. 3, which is in fluid communication with the interior of the inflatable member 16 and the annular lumen 14. Upon inflation, the distal section 17 expands, as shown in phantom in FIG. 3 causing the transverse dimensions of the lumen 20 to increase. Upon removal of inflation fluid both the distal section 17 and the inflatable member 16 elasticly recoil back to essentially their original preinflation sizes and shapes. The deflated condition after inflation may be slightly larger than prior to the initial inflation. The distal section 17 is shown in FIG. 3 with its inner periphery taking the shape of the exterior of inner tubular member 11 but being unsecured to the inner tubular member. FIG. 3A illustrates the distal section 17 in an alternative embodiment where the outer tubular member 13 forming the distal section 17 takes the shape of the inner tubular member 11 member and where a substantial part of the inner periphery of the distal section is also secured to the exterior of the inner tubular member 11. The inflation lumen 20A is shown in this embodiment as having a thin arcuate transverse shape in an uninflated condition, but which, as shown in phantom, expands to form a crescent shaped inflation lumen 20A upon inflation. Only the expandable part of the outer tubular member 13 needs to be heat treated in accordance with the invention.

The use of the dilatation catheter shown in FIGS. 1–5 generally follows conventional PTCA practices with over-the-wire dilatation catheters as described in the BACKGROUND OF THE INVENTION. The proximal end of guidewire 21 is backloaded into the inner lumen 12 of the inner tubular member 11 of the catheter body 10 and both the guidewire and the catheter are advanced together through a guiding catheter (not shown) which has been previously disposed within the patient's arterial system, with the distal end of the guiding catheter seated within the ostium of the desired coronary artery and the proximal end thereof extending out of the patient. The guidewire 21 is first advanced out the distal end of the guiding catheter into the patient's coronary artery until its distal extremity extends beyond the lesion to be dilated, and then the dilatation catheter is advanced over the guidewire, which is being held in its position, until the inflatable member 16 on the dilatation catheter is properly disposed within the stenotic region so that the lesion can be dilated upon the inflation thereof. After the dilatation, the inflatable member 16 is deflated and the catheter and the guidewire are withdrawn from the patient. If further treatment or diagnosis is to be conducted, the guidewire 21 can be replaced with an exchange wire before removing the dilatation catheter so that the first catheter can be removed and another advanced into the desired location over the exchange wire or an extension wire can be attached to the proximal end of the guidewire in place to perform essentially the same function. See the discussion of exchange wires and extension wires in U.S. Pat. No. 4,827, 941 (Taylor et al.) which is incorporated herein by reference.

FIGS. 6–10 schematically illustrate another dilatation catheter embodying features of the invention which is adapted for rapid exchange during an angioplasty procedure. The catheter includes a catheter shaft 30 having a distal shaft section 31 and a proximal shaft section 32. The proximal section 32 has an outer plastic tubular jacket or coating 33 which fits tightly, e.g. is shrunk fit, onto a high strength tubular element 34 which may be formed of hypotubing. The distal section 31 also includes an expandable outer tubular member 35 which is disposed about the inner tubular member 36 with a very thin annular inflation lumen 37 disposed between the inner and outer tubular member when the latter is in an uninflated condition. As shown in phantom in FIGS. 6, 9 and 1 0, upon the introduction of inflation liquid under pressure into the lumen 37, the outer tubular member 35 expands along with the inflatable member or balloon 38 as shown. Upon the withdrawal of the inflation fluid, the outer tubular member 35 and the inflatable member 38 contract by elastic recoil to a much smaller outer transverse dimension, usually the same size or just slightly larger than the original uninflated dimensions.

The outer tubular member 35 may be an elongated proximal skirt of the inflatable member 38, as shown in FIG. 6, or it may be a separate tubular member with the proximal skirt of the inflatable member 38 bonded to the distal end of the separate tubular member. The inflatable member 38 is secured by its distal end or skirt to the distal end of the inner tubular member 36 by suitable means such as heat shrinking or by heat or adhesive bonding. The annular inflation lumen 37 defined between the distal section 35 and the inner tubular member 36 is in fluid communication with inflation lumen 40 in the proximal section 32 and the interior of the inflatable member 38. The expanded inflated state of the distal section 35 shown in phantom provides for a very rapid inflation and deflation of the inflatable member 38.

Guidewire 41, which may be of conventional construction, extends through the inner lumen 42 of the inner tubular member 36 and out the proximal guidewire port 43 in the proximal end of the inner tubular member and a distal guidewire port 44 in the distal end of the inner tubular member. A flexible coil 45 is provided on the distal end of the guidewire 41.

The outer tubular member 35 is bonded to the lower exterior portion of the inner tubular member 36 by suitable means such as heat bonding or adhesives and a slit is 46 is provided through the bonded walls thereof from the proximal guidewire port 43 to a more distal location 47 to facilitate removal of the guidewire.

The high strength tubular element 34 of the proximal section 32 of the shaft 30, onto which the outer plastic jacket 33 is secured, is preferably hypotubing and may be formed of conventional stainless steel or a NiTi alloy, particularly a NiTi alloy which is in a stable austenite phase at body temperature which exhibits stress induced martinsite formation such as described in copending applications Ser. No. 08/071,322, filed Dec. 18, 1990, entitled SUPERELASTIC GUIDING MEMBER; Ser. No. 07/994,679, filed Dec. 22, 1992, and Ser. No. 08/212,431, filed Mar. 11, 1994, entitled SUPERELASTIC GUIDING MEMBER, which are incorporated herein in their entirety by reference.

The catheter construction of this embodiment with a relatively short inner lumen 42 adapted to slidably receive the guidewire 41, eliminates the need for using an exchange wire or a guidewire extension, as described in the Yock and Horzewski et al. patents. A dual lumen type catheter shaft construction such as described in Horzewski et al. may also be used in the portion of the catheter proximal to the proximal guidewire port 43.

There are at least two modes of inserting the dilatation catheter of the embodiment shown in FIGS. 6–10 into the patient's coronary anatomy. The first method is for the most part the same as in the prior over-the-wire embodiment, namely, the guidewire 41 is preloaded into the short inner lumen 42 of the inner tubular member 36 and both are advanced through a guiding catheter (not shown) previously disposed within the patient's arterial system with the distal end of the guiding catheter seated within the ostium of a coronary artery as described in the BACKGROUND OF THE INVENTION. The second mode, frequently called the "bare wire" technique, involves first advancing a guidewire 41 through the guiding catheter and out the distal end thereof until it is positioned within the patient's coronary artery across the lesion to be dilated. The proximal end of the guidewire 41, which is outside the patient, is backloaded, i.e. inserted, through the distal guidewire port 44 into the short inner lumen 42 of the inner tubular member 36 and advanced proximally therein until it exits the proximal guidewire port 43. The proximal end of the guidewire 41 is held in place while the catheter is advanced over the guidewire through the patient's vascular system until the dilatation balloon 38 on the catheter is positioned across the stenotic region so that the stenosis will be dilated upon the inflation of the balloon. After the dilatation of the lesion, the balloon 38 is deflated and then the catheter may be removed from the patient's artery. If other diagnostic or therapeutic procedures are contemplated or are possible, the catheter is slidably removed over the guidewire 41, leaving the guidewire in place, so that other catheters can be advanced over the inplace guidewire in a similar manner without the need for exchange wires or guidewire extensions.

FIGS. 11 through 15 illustrate yet another dilatation catheter embodying features of the invention which provides for the perfusion of blood distal to the catheter during the dilatation of a stenotic lesion. The catheter includes the catheter shaft 50, an inner tubular member 51 which has an inner lumen 52, and an outer tubular member 53 which is disposed about the inner tubular member and which defines an annular inflation lumen 54 located between the inner and outer tubular members in the proximal portion of the catheter shaft. An adapter 55 is secured to the proximal ends of the inner and outer members 51 and 53. An inflatable member or balloon 56 is secured by its distal end to the distal end of the inner tubular member 51. The outer tubular member 53 has an expandable distal section 57 which is partially bonded along a length 58 thereof to the exterior of the inner tubular member 51 as previously described in the embodiment shown in FIGS. 6–10, forming the arcuate inflation lumen 59. The expandable distal section 57 expands upon the introduction of inflation liquid into the arcuate inflation lumen 59 expanding it into a crescent shape shown in phantom in FIG. 13 and directs inflation fluid to the interior of inflatable member 56.

As shown in FIGS. 11–15, a plurality of perfusion ports 60 which pass through the bonded walls of the inner tubular member 51 and the expandable distal section 57 respectively proximal to the inflatable member 56 and which are in fluid communication with the inner lumen 52 of the inner tubular member 51. Additionally, one or more perfusion ports 63 are provided distal to the inflatable member 56 through the wall of the inner tubular member 51 and are in fluid communication with the inner lumen 52 extending therein. In this manner, when the inflatable member 56 is inflated during an angioplasty procedure, oxygenated blood is forced to pass through the proximal perfusion ports 60, through the inner lumen 52 and then out the distal perfusion ports 63 to provide oxygenated blood distal to the catheter and thereby avoid the generation of ischemic conditions in tissue downstream thereof or the aggravation of existing ischemic conditions. The transverse dimensions of the inner tubular member 51 within the bonded section are preferably larger than in the embodiments previously discussed to allow for an increased flow of blood therethrough.

The use of the embodiment shown in FIGS. 11–15 is essentially the same as the embodiment shown in FIGS. 1–5. The only essential difference is that the inflatable member 56 of the embodiment shown in FIGS. 11–15 can be inflated for significantly longer periods, e.g. typically about 20–30 minutes but possibly up to 5 hours or more, than the first described embodiment because oxygenated blood is flowing to the tissue distal to the inflated balloon.

The dilatation catheter shown in FIGS. 11–15 may be modified by providing a guidewire port at the proximal to the expandable distal section 57, as shown in FIGS. 6–10. However, the guidewire port should be spaced sufficiently far proximally from the portion of the bonded distal section 57 having the perfusion ports 60 so that the guidewire can be pulled proximally and remain within the inner lumen 52 while the balloon 56 is inflated during the dilatation but not interfere with the flow of blood through the perfusion ports 60 and 63 and the inner lumen 52. Alternatively, means can be provided within the inner lumen 52 proximal to the perfusion ports 60 to grasp the guidewire to hold the guidewire in position while blood passes through the inner lumen 52. After the angioplasty procedure is completed, the guidewire can then be advanced distally through the inner lumen 52 and out the distal end thereof in order to maintain access to the lesion in case further treatment or diagnosis is necessary or desirable.

The above described catheters may be made by conventional techniques well known to those skilled in the art such as references incorporated herein by reference. The various components of the catheters and guidewires of the invention, unless otherwise discussed, can be formed from a wide variety of conventional materials. The catheter shaft proximal to the expandable distal section may be made from a variety of polymeric materials including polyethylene, polyimide, polyvinyl chloride and zinc, lithium and sodium olefinic ionomers, such as Surlyn® sold by E. I. DuPont, deNemours & Co. The balloon and the distal portion of the outer tubular member which forms the inflatable unbonded portion may be made from polyethylene, polyethylene terephthalate, olefinic ionomers and other relatively inelastic polymers and other materials, as described in the aforementioned application Ser. No. 07/758,630.

The dimensions of the catheters of the invention generally follow the dimensions of conventional intravascular catheters. For coronary angioplasty the length is typically about 135 cm and the outer diameter of the outer tubular member is about 0.02 to about 0.06 inch. In a presently preferred embodiment, the distal expandable section is long enough (e.g. preferably about 10 to about 40 cm) to ensure that it is the only portion of the catheter shaft proximal to the balloon which exits the guiding catheter and enters the patient's coronary anatomy during intravascular procedures. The transverse dimensions of the catheter may be larger with catheters for use in peripheral arteries and other locations. The thicknesses of the expandable distal section depends upon the desired mechanical properties for this material.

The following example is given to further illustrate features of the invention. An outer tubular member for a dilatation catheter was prepared having a structure essentially as shown in FIGS. 1–3 and made of Surlyn® (8020 grade), a zinc ionomer supplied by the E. I. DuPont, deNemours & Company. The outer tubular member had an OD of about 0.037 inch (0.94 mm) and an ID of about 0.025 inch (0.61 mm), i.e. a wall thickness of about 0.006 inch (0.15 mm) over essentially its entire length. The outer tubular member 14 was irradiated (gamma radiation) at a level of about 45 to 55 mrads in order to cross-link essentially the entire polymeric tube. The distal portion of the polymerized tubular member which was to become the expandable distal portion was subjected to a thermal treatment at about 250° F. for a period of about 20 seconds while applying tension in the longitudinal direction in order to develop a significant level of longitudinal orientation in the inflatable portion. After the thermally treated inflatable portion of the tubular member had cooled to room temperature, the dilatation catheter 10 was assembled. The relationship between the outer diameter of the expandable section and the fluid pressure is represented in FIG. 16 by curve A. As is evident, at pressures from up to about 8 atmospheres, the change in the outer diameter of the inflatable section is relatively small, indicating that the material has little compliance within this pressure range. At pressures from about 8 to about 12 atmospheres there is a substantial expansion in the elastic mode. At internal pressures above about 12 atmospheres the expansion of the expandable section 17 was quite small, i.e. it was relatively noncompliant, and the expansion was essentially linear with respect to the interior pressure within the inflatable section. Upon deflation, the tubular section elasticly contracts to a much smaller transverse cross section, preferably to essentially the same starting transverse dimensions.

The following example is given to illustrate another presently preferred embodiment of the invention. Pellets of a lithium olefinic ionomer such as Surlyn 7930 or 7940 are extruded at a temperature of about 350° F. to about 450° F. into tubular stock. Upon exiting from the extrusion die, the tubular stock is quenched in a trough of cool water, preferably about 45°–55° F., in order to obtain a highly amorphous material. The cooled tubular product is stabilized at about 40° F. to 80° F., typically about 60° F. for about 2 to about 6 hours, typically about 4 hours. The portion of the stabilized tubular product which is to be formed into the expandable distal section is then irradiated at about 45 to about 75 Mrads, preferably about 55 to about 65 Mrads. The tubular product is then subjected to an internal pressure of about 50 to about 85 psi, preferably about 60 to about 75 psi, at a temperature of about 225° F. degrees to about 250° F. to expand or blow the irradiated portion of the tubular member. The expanded tubular section is assembled with other components into a catheter and then it is heat treated at about 55° C. to about 65° C. for about 10 to about 30 minutes to heat shrink the expanded section to a diameter the same or slightly larger than its original diameter. This embodiment provides an expandable distal section which expands significantly in the elastic mode within pressure range much lower than the first discussed embodiment, The curve B in FIG. 16 illustrates the expansion of the distal section formed in the above manner at various interior pressures. The starting point of curve B, as shown, is after expanded section has been inflated with sufficient inflation liquid to be relatively wrinkle free. As indicated by curve B, the expansion begins at about 2 atmospheres and continues at a relatively constant rate to about 8 atmospheres. The expansion of the distal section is relatively high and in the elastic mode but the rate of expansion is lower than that of the first example and the expansion occurs over a larger pressure range than in the first example. At a pressure level of about 10 atmospheres and beyond, the expansion of the inflatable member is relatively low, i.e. the inflatable member is relatively noncompliant. Upon deflation of the inflated member, the diameter of the inflatable member follows the expansion rates shown in the drawing to essentially the starting point.

Various modifications can be made to the present invention. For example, with the aforementioned preferred embodiment only the distal portion of the outer tubular member 14 that was to form the expandable distal section 17 was subjected to the heat treatment. If desired, the entire outer tubular member 14 can be given a thermal treatment to develop the characteristics of elastic expansion but the exterior of the non-inflatable portion of the outer tubular member may be provided with an inelastic jacket or coating so that only the inflatable section 16 inflates when subjected to internal pressure. Other modifications include forming the inflatable section of an outer tubular member in accordance with the invention and secure the inflatable section to a catheter shaft of different material or the same material with differing properties. The preexpansion of the expandable distal section during the thermal treatment before heat shrinking the expanded section also decreases the rate of increase of the expansion, but it does not substantially change the second pressure range in which the material is relatively noncompliant.

The distal sections of the outer tubular members may be formed by heat shrinking them with some means such as a mandrel between the inner and outer tubular members to form the expandable unbonded portion. A fusion bond between the inner and outer tubular members is preferred, particularly in those embodiments which have perfusion ports which pass through the bonded walls, because such bonds prevent delamination of the bonded walls. A mandrel may be inserted into the inner lumen of the inner tubular member to support the latter during the heat bonding of the outer tubular member thereon. Alternate methods may be employed to make the distal section. For example, the distal part of the outer tubular member may be preformed into the desired shape and then be adhesively bonded to the exterior of the inner tubular member.

While the invention has been described herein primarily in terms of catheters for coronary angioplasty, the invention may be employed in a wide variety of catheters for insertion into various body lumens. Additionally, modifications and improvements can be made to the invention without departing from the scope thereof.

What is claimed is:

1. An intraluminal catheter comprising:
   a) an elongated catheter shaft having proximal and distal shaft portions and a first tubular member in the distal shaft portion which elastically expands substantially at least in part upon inflation to a pressure within a first pressure range and expands very little in a second higher pressure range, which contracts by elastic recoil upon deflation to a deflated diameter much smaller than the inflated diameter, and which defines at least in part an expandable inflation lumen extending through the distal shaft portion; and
   b) an inflatable member on the distal shaft portion having an interior in fluid communication with the expandable inflation lumen.

2. The intraluminal catheter of claim 1 including a second tubular member disposed within the inner lumen of the distal shaft portion and together with the distal shaft portion defines the expandable inflation lumen.

3. The intraluminal catheter of claim 2 wherein the inner tubular member and the expandable distal portion of the outer tubular member are secured together along a length thereof and the expandable inflation lumen defined therebetween has a crescent-shaped transverse cross-section.

4. The intraluminal catheter of claim 2 wherein the second tubular member as a distal end, a guidewire port in the distal end, a guidewire receiving inner lumen extending therein to the guidewire port in the distal end of the second tubular member.

5. The intraluminal catheter of claim 4 wherein the inflatable member has a distal end secured to the distal end of the second tubular member.

6. The intraluminal catheter of claim 4 including a guidewire port in the catheter shaft which is in fluid communication with the inner lumen of the second tubular member and which is spaced a short distance proximally from the inflatable member and a substantial distance distally from the proximal end of the catheter shaft.

7. The intraluminal catheter of claim 2 wherein a substantial part of the first tubular member takes the shape of and is secured to an exterior part of the second tubular member along a length thereof.

8. The intraluminal catheter of claim 2 wherein about 30 to about 90% of the first tubular member takes the shape of and is secured to an exterior part of the second tubular member along a length thereof.

9. The intraluminal catheter of claim 1 wherein the first tubular member in the distal shaft portion is formed of an olefinic ionomer.

10. The intraluminal catheter of claim 9 wherein the olefinic ionomer is a sodium, zinc or lithium ionomer.

11. The intraluminal catheter of claim 1 including means on the proximal end of the shaft to direct inflation fluid at elevated pressure from a source through the inflation lumen in the catheter shaft to expand the expandable inflation lumen in the distal shaft section to facilitate the flow of inflation fluid to the interior of the balloon.

12. The intraluminal catheter of claim 1 wherein the outer diameter of the distal shaft section has a first diameter in a deflated condition and upon inflation expands to a second diameter which is about 5 to about 50% greater than first diameter.

13. The intraluminal catheter of claim 1 wherein the outer diameter of the distal shaft portion has a first diameter in a deflated condition and upon inflation expands to a second diameter which is about 10 to about 30% greater than the first diameter.

14. The intraluminal catheter of claim 1 wherein the inflatable member and first tubular member are formed in a one piece construction from the same polymeric material.

15. The intraluminal catheter of claim 1 wherein the inflatable member is formed independently of the outer tubular member and has a proximal end secured to a distal portion of the first tubular member.

16. A balloon dilatation catheter comprising:
   a) an elongated catheter shaft having proximal and distal shaft portions and a first tubular member in the distal shaft portion which at least in part expands substantially in an elastic mode to an inflated diameter upon inflation to a pressure within a first pressure range and expands very little in a second higher pressure range, which contracts by elastic recoil upon deflation to a deflated diameter much smaller than the inflated diameter, and which defines at least in part an expandable inflation lumen extending through the distal shaft portion; and
   b) a dilatation balloon on the distal shaft portion having an interior in fluid communication with the expandable inflation lumen.

17. An elongated catheter for performing intraluminal therapeutic or diagnostic procedures, comprising:

a) an inner tubular member having a first inner lumen and a distal end with a port in communication with the first inner lumen; and b) an outer tubular member disposed about the inner tubular member having about 30 to about 90% of an inner periphery thereof which takes the shape of and is secured to the exterior of the inner tubular member along a length thereof and an unsecured portion of the outer tubular member being elastically expandable so that when inflated it elastically expands and defines a second inner lumen extending longitudinally between the inner and outer tubular members.

18. The elongated catheter of claim 17 including a second guidewire receiving port which extends through the secured sections of the outer tubular member and the inner tubular member and which is in communication with the first inner lumen of the inner tubular member.

19. The elongated catheter of claim 17 including therapeutic or diagnostic means at a location distal to the length of the inner tubular member where the outer tubular member is secured thereto.

20. The elongated catheter of claim 19 wherein the therapeutic or diagnostic means is an expandable dilatation member provided on the distal end of the catheter.

21. The elongated catheter of claim 20 wherein the expandable member is an inflatable balloon with an interior in fluid communication with the second inner lumen between the inner and outer tubular members.

22. The elongated catheter of claim 17 wherein a portion of the catheter body proximal to the secured portion is stiffer than the secured portion.

23. The elongated catheter of claim 22 wherein a portion of the outer tubular member proximal to the secured portion thereof is formed of hypotubing to increase the stiffness of the inner tubular member.

24. A dilatation catheter for performing angioplasty procedures within a patient's arterial system comprising:

a) an elongated catheter shaft having a distal section which includes an outer tubular member disposed about the inner tubular member with about 30 to about 90% of an inner periphery thereof taking the shape of and being secured to the exterior of the inner tubular member along a length thereof and with an unsecured portion thereof being elastically expandable so that when inflated it defines an expanded second inner lumen extending longitudinally between the inner and outer tubular members;

b) an inflatable dilatation member on the catheter shaft distal to the secured section of the outer tubular member having an interior in fluid communication with the second inner lumen and having a distal end secured to the distal end of the inner tubular which extends through the interior of the balloon; and c) means to direct inflation fluid from a source through the second inner lumen to the interior of the balloon.

25. The elongated catheter of claim 24 including a second guidewire receiving port which extends through the secured sections of the inner tubular member and the outer tubular member and which is in communication with the first inner lumen of the inner tubular member.

26. The dilatation catheter of claim 24 wherein the outer tubular member is secured to the inner tubular member by heat bonding or adhesive bonding.

27. A balloon dilatation catheter comprising:

a) an elongated catheter shaft having proximal and distal portions and a first tubular member in the distal portion thereof which expands at least in part substantially in an elastic mode upon inflation to a pressure within a first pressure range and expands very little in a second higher pressure range, which contracts by elastic recoil upon deflation to a deflated diameter and which defines at least in part an expandable inflation lumen extending through the distal portion of the catheter shaft; and b) a dilatation balloon on the distal portion of the elongated shaft having an interior in fluid communication with the expandable inflation lumen.

\* \* \* \* \*

UNITED STATES PATENT AND TRADEMARK OFFICE
CERTIFICATE OF CORRECTION

PATENT NO. : 5,533,968
DATED : July 9, 1996
INVENTOR(S) : K. Muni et al.

It is certified that error appears in the above-indentified patent and that said Letters Patent is hereby corrected as shown below:

Column 12, line 40, after "than" insert --the--; and

Column 14, line 14, after "tubular" insert --member--.

Signed and Sealed this

Fourth Day of November, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO. : 5,533,968
DATED : July 9, 1996
INVENTOR(S) : K. Muni et al.

It is certified that error appears in the above-indentified patent and that said Letters Patent is hereby corrected as shown below:

Column 14, line 14, after "tubular" insert --member--.

Signed and Sealed this

Twenty-second Day of June, 1999

Attest:

Q. TODD DICKINSON

Attesting Officer     Acting Commissioner of Patents and Trademarks